United States Patent
Chiang et al.

[11] Patent Number: 5,246,706
[45] Date of Patent: Sep. 21, 1993

[54] DEVICE FOR ADMINISTERING BIMAKALIM TRANSDERMALLY

[75] Inventors: Chia-Ming Chiang, Foster City; Tung F. Chen, Redwood City, both of Calif.

[73] Assignee: Cygnus Therapeutic Systems, Redwood City, Calif.

[21] Appl. No.: 733,729

[22] Filed: Jul. 19, 1991

[51] Int. Cl.$^5$ .............................................. A61F 13/00
[52] U.S. Cl. ........................................ 424/449; 424/448; 514/277; 514/947
[58] Field of Search ........................... 424/448, 449

[56] References Cited

U.S. PATENT DOCUMENTS

| | | | |
|---|---|---|---|
| 4,421,737 | 12/1983 | Ito | 424/448 |
| 4,615,699 | 11/1986 | Gale | 424/448 |
| 4,655,767 | 4/1987 | Woodard | 424/448 |
| 4,752,478 | 6/1988 | Bondi | 424/448 |
| 4,906,463 | 3/1990 | Cleary et al. | 424/78 |
| 5,006,342 | 4/1991 | Cleary et al. | 424/445 |
| 5,061,813 | 11/1991 | Atwal | 544/151 |

FOREIGN PATENT DOCUMENTS 9103219  3/1991  PCT Int'l Appl.

Primary Examiner—Thurman K. Page
Assistant Examiner—D. Gabrielle Phelan
Attorney, Agent, or Firm—Morrison & Foerster

[57] ABSTRACT

Multi-day skin patches for administering bimakalim transdermally to treat cardiovascular diseases are described which consist of laminated composites having an occlusive elastomeric polymer backing layer and an underlying reservoir layer composed of a solid matrix of bimakalim dispersed in a polydimethylsiloxane or acrylate adhesive. The skin flux of bimakalim from the patches is greater than 0.1 $\mu g/cm^2/hr$.

11 Claims, 1 Drawing Sheet

DEVICE FOR ADMINISTERING BIMAKALIM TRANSDERMALLY

TECHNICAL FIELD

This invention relates to devices in the form of laminated composites for administering the drug bimakalim or its potassium channel activating analogs transdermally.

BACKGROUND

Bimakalim is a potassium channel activating drug that is useful for treating coronary heart disease. The chemical structure of bimakalim (4-(1,2-dihydro-2-oxo-1-pyridyl)-2,2-dimethyl-2H-1-benzopyran-6-carbonitrile) is as follows:

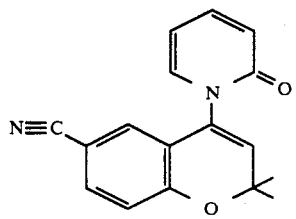

It is a nonionizable neutral molecule which in its pure form is a white crystalline powder that melts at 148° C. It is known to have a water solubility of approximately 0.7 mg/ml and a partition coefficient of 27.0 (octanol/-phosphate buffer, pH 7.4). Its derivative, (−)-trans-3,4-dihydro-4-(1,2-dihydro-2-oxo-1-pyridyl)-3-hydroxy-2,2-dimethyl-2H-1-benzopyran-6-carbonitrile, in which the double bond between the 3- and 4-position carbon atoms of the benzopyran group is absent and the 3-position carbon atom is substituted with a hydroxy group, also exhibits potassium channel activating properties.

Bimakalim has heretofore been administered orally and parenterally. The effective dose for treatment of cardiovascular disease is normally in the range of 0.2 to 1 mg/day. There has been no reported transdermal administration of bimakalim or its derivatives nor has there been any report of whether it is capable of permeating through human skin at rates which are practical for transdermal delivery.

Numerous patent publications describe laminated composites for administering drugs transdermally in which the drug is dispersed in a matrix of a pressure sensitive adhesive. See, for example, U.S. Pat. Nos. 4,906,463 and 5,006,342 and PCT Publication WO91/03219. The inclusion of molecules such as propylene glycol monolaurate (PGML) in the matrix that increase the solubility of drug in the adhesive and/or provide skin permeation enhancement is known. See, for instance, the above-cited patent publications.

DISCLOSURE OF THE INVENTION

The invention is a multi-day device or patch for administering bimakalim or its potassium channel activating derivatives transdermally in amounts sufficient to treat indications that are treatable with potassium channel activation, such a cardiovascular disease, hypertension, asthma or urogenital malfunction. The patch is in the form of a laminated composite having at least two layers:

(a) an occlusive polymeric backing layer and (b) an underlying reservoir layer comprising a solid matrix of bimakalim or a derivative thereof dispersed in a pharmaceutically acceptable adhesive through which the bimakalim or derivative is capable of diffusing, wherein the flux of bimakalim or derivative from the device is at least about 0.1 $\mu g/cm^2/hr$, and the amount of bimakalim or derivative in the device and the drug delivery area of the device are sufficient to provide a therapeutically effective level of bimakalim or derivative over the multi-day period.

In preferred embodiments of the device, the reservoir layer serves as the basal layer of the device and is in direct drug-delivery contact with the skin during use. The device will also typically include a removable release liner layer underlying the reservoir layer which is removed prior to application of the patch to the skin.

BRIEF DESCRIPTION OF THE DRAWING

The drawing is an elevated cross-sectional depiction of one embodiment of the patch of the invention. The drawing is not to scale.

MODES FOR CARRYING OUT THE INVENTION

Figure 1:
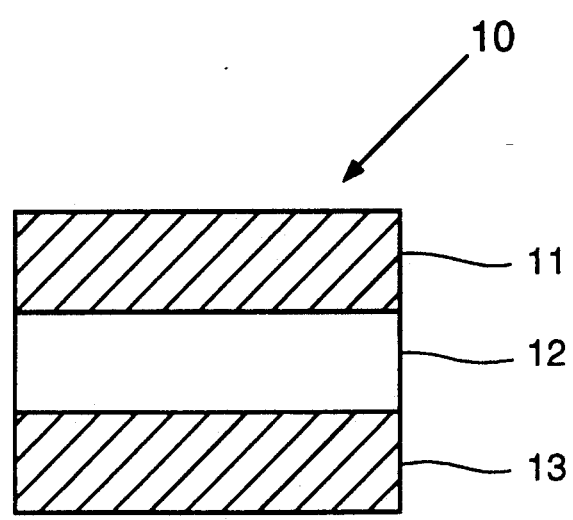

As used herein the term "flux" intends the rate per unit area at which bimakalim or its derivatives permeate through skin as measured in vitro by the procedure described in the examples, infra.

The term "drug delivery area" as used herein intends the area of skin through which bimakalim from the device passes. The drug delivery area will usually be equivalent to the basal surface area of the reservoir layer.

As used herein, the term "transdermal" intends both percutaneous and transmucosal administration, i.e., passage of bimakalim or its pharmaceutically active derivatives or analogs through intact unbroken skin or mucosal tissue into circulation.

As used herein the terms "cardiovascular disease" or "coronary heart disease" intend disorders or diseases of the heart and/or blood vessels and includes, without limitation, diseases of inflammatory origin, angina pectoris, arteriosclerotic cardiopathy, fatty cardiopathy, hypertensive cardiopathy, nephropathic cardiopathy, and toxic cardiopathy.

As used herein the term "therapeutically effective" intends that dose of bimakalim/derivative that alleviates or corrects the particular indication being treated. It will be appreciated that the dose may vary with the individual and/or condition being treated.

The drawing shows perhaps the simplest embodiment of the invention. The depicted patch, generally designated 10 consists of three layers: a top backing layer 11; an underlying reservoir layer 12 composed of a matrix of bimakalim dispersed in a pressure sensitive adhesive; and a release liner layer 13.

Since the patch is intended to be worn by the patient for a multiplicity of days, typically 1 to 7 days, the backing is preferably made of one or more layers of elastomeric polymer(s) that allow the device to be resilient and flexible. The backing layer is also preferably occlusive (i.e., it precludes transmission of water vapor from the skin) and is substantially impermeable to the components of the reservoir layer. Examples of elastomeric polymers from which the backing layer may be made are polyurethanes, polyisobutene, styrene-butadiene, and other rubber-type elastomers. The thickness of the backing layer will normally be 10 to 100 microns, more usually 12.5 to 75 microns.

The reservoir layer is a matrix of the drug dispersed in the adhesive. The layer is a "solid-state" type matrix in that it does not exhibit any significant fluidity at normal storage and use temperatures. Any of the various pharmaceutically acceptable adhesives commonly used in transdermal drug-delivery patches may be employed, although silicone-based (polydimethylsiloxane) and acrylate polymeric adhesives are preferred. In any event the adhesive must be of a nature to permit the bimakalim to dissolve therein and diffuse therethrough to the skin.

The bimakalim is present in the layer in excess (i.e., it exists in both dissolved and undissolved form). The amount of bimakalim in the reservoir layer must be sufficient to provide the necessary daily amount required for therapy over the intended effective lifetime of the patch. Accordingly, there will typically be in the range of 5 to 20 mg bimakalim in the reservoir layer. These amounts will normally constitute 1 to 10% by weight of the reservoir layer. Depending upon the inherent solubility of the bimakalim in the adhesive and the desired flux, it may be necessary or desirable to include compounds in the matrix that increase the solubility of bimakalim/derivative in the adhesive and/or facilitate the permeation of bimakalim/derivative through the skin. For instance, when certain solvent-based acrylate adhesives are used in the matrix, no additive is normally needed to achieve the desired flux levels. On the other hand, when polydimethylsiloxane adhesives are used, it is necessary to include molecules such as PGML, methyl laurate, oleic acid, vegetable oils and other known solubilizers/permeation enhancers to achieve higher skin fluxes. When used, the additive will usually constitute 1 to 15% by weight, more usually 2 to 12% by weight, of the reservoir layer. The exact amount will depend upon the particular additive.

The thickness (dry) of the reservoir layer is not critical and will usually be in the range of 75 to 200 microns, more usually 100 to 150 microns.

In the embodiment shown in the drawing, the lower surface of the reservoir layer defines the basal surface of the patch and the drug-delivery area. Since the reservoir layer is composed of an adhesive matrix, this surface also provides the means by which the patch is affixed to the skin. In such embodiments, the reservoir preferably includes hydrophilic polymers that absorb water such as polyvinylpyrollidone, gelatin or Microcel C to facilitate long wearing.

The release liner layer 13 serves to prevent the bimakalim in the reservoir layer from being released to other surfaces (e.g., packaging during storage or skin or clothing after the patch has been removed from its package). The use of such a layer is common in the art. This layer is normally made of an impermeable polyester coated with a release coating (e.g., Teflon polymer or silicone oil). As indicated above, this layer is peeled or otherwise removed from the patch prior to application of the patch to the skin.

The patch may include one or more additional layers or components such as spaced resilient structural layers or nonwoven fabric to provide structural support or membranes underlying the reservoir to regulate the release of drug. If such underlying layers are employed, other means, such as an underlying adhesive layer or peripheral adhesive layer, may be used to affix the patch to the skin.

The respective layers of the patch may be assembled and laminated together using conventional mixing or blending and lamination techniques. Patches of the desired size may be cut or punched from bulk laminated composite stock.

The following examples further illustrate the invention. They are not intended to limit the invention in any manner. Percentages are by weight unless indicated otherwise.

Example 1

Prototype laminated composites using a polydimethylsiloxane (PDMS) adhesive (Dow Corning #2675) were prepared and tested as follows.

Bimakalim alone or in combination with various solubilizers/permeation enhancers were mixed in a rotating vessel at 25° C. for 1–3 hr. A 100 micron thick drug reservoir lamina was made by laminating the mixture on a polyester release liner (3M #1022) with a 15 mil knife. The solvent in the PDMS was removed by heating the assembly in an oven at 70° C. for 30 min. After cooling the reservoir/release liner assembly was laminated to a 75 micron thick polyester backing layer.

In vitro skin flux tests of the prototypes were carried out using modified Franz flow-through cells. Human cadaver skin was used. Frozen skins were thawed and epidermal layers (stratum corneum and viable epidermis) were separated from the full-thickness skin by immersion in water at 60° C. for 2 minutes. The release liner layer was removed from the prototype and the prototype was placed on top of the epidermis with the reservoir layer facing the stratum corneum. Gentle pressure was applied. The skin membrane with the prototype affixed thereto was then mounted between the two half-cells and fastened with a clamp. The receiver compartment was filled with phosphate buffered saline pH 7.4 and maintained at 32° C. Samples were taken from the receiver compartment at preset intervals and assayed by HPLC. Flux was calculated from the slope of the cumulative amounts of bimakalim in the receiver compartment versus time.

Table 1 below presents further details and the results of these flux studies (ML=methyl laurate; veg. oil=-vegetable oil, PG=propylene glycol; S.O.=silcone oil, Dow Corning #355).

TABLE 1

| | | Flux ($\mu g/cm^2/hr$) | |
|---|---|---|---|
| % Bimakalim | % Additive | Skin 1 | Skin 2 |
| 1 | — | 0.25 ± 0.04 | |
| 1 | 4 - PGML | 0.70 ± 0.07 | 1.07 ± 0.12 |
| 3 | 4 - PBML | | 1.43 ± 0.17 |
| 1 | 8 - PGML | | 2.23 ± 0.08 |
| 1 | 3 - veg. oil | 0.83 ± 0.32 | 1.36 ± 0.07 |
| 1 | 6 - veg. oil | | 1.55 ± 0.12 |
| 1 | 2 - oleic acid 2 - veg. oil | | 2.79 ± 0.28 |
| 1 | 3 - ML 3 - PG | | 0.53 ± 0.06 |
| 1 | 3 - PGML 3 - PG | | 1.71 ± 0.62 |
| 1 | 4 - S.O. | | 0.25 ± 0.00 |

Example 2

A prototype was produced as in Example 1 except that the PDMS was replaced with a solvent-based acrylate adhesive (Morton-Thiokol, Morstik 607; approximately 85% 2-ethylhexylacrylate, 10% methylacrylate, 3% acrylic acid, 2% vinyl acetate). The amount of bimakalim in the reservoir was 5%.

Flux studies were conducted as in Example 1 on four skin samples. Table 2 below presents the results of those studies.

TABLE 2

| Skin # | Flux ($\mu g/cm^2/hr$) |
|---|---|
| 1 | 1.78 ± 0.15 |
| 2 | 1.04 ± 0.10 |
| 3 | 1.18 ± 0.06 |
| 4 | 0.87 ± 0.04 |

Example 3

Two prototypes were produced as in Example 1 except that the PDMS was replaced with a water-based acrylate adhesive (Air Products, Flexcryl 1625). The amounts of bimakalim in the prototypes were 1% and 5%. Skin flux studies were conducted as in Example 1. The results are shown in Table 3.

TABLE 3

| Skin # | % Bimakalim | Flux ($\mu g/cm^2/hr$) |
|---|---|---|
| 1 | 1 | 0.48 ± 0.07 |
| 2 | 5 | 1.54 ± 0.29 |

Example 4

Prototypes were prepared as in Example 1 containing, respectively, 1% bimakalim and either 4% or 8% PGML and tested for seven days. Each prototype was tested on three skin samples. The prototypes containing 4% PGML exhibited an average flux over 144 hr of 0.683±0.18 $\mu g/cm^2/hr$ whereas the prototypes containing 8% PGML exhibited an average flux over that time of 1.04±0.31 $\mu g/cm^2/hr$.

Modifications of the above-described modes for carrying out the invention that are obvious to those of ordinary skill in the field of transdermal drug delivery are intended to be within the scope of the following claims.

We claim:

1. A multi-day patch for administering bimakalim or a pharmaceutically active derivative thereof transdermally in amounts sufficient to treat a cardiovascular disease, hypertension, asthma or urogenital malfunction, the patch being in the form of a laminated composite comprising:
   (a) an occlusive polymeric backing layer; and
   (b) an underlying reservoir layer comprising a solid matrix of 5 to 20 mg of bimakalim or a pharmaceutically active derivative thereof disposed in a pharmaceutically acceptable polymer adhesive through which the bimakalim or derivative is capable of diffusing,
   wherein the skin flux of bimakalim or derivative from the patch is at least about 0.1 $\mu g/cm^2/hr$ and the amount of bimakalim or derivative in the patch and the drug-delivery area of the patch are sufficient to provide a therapeutically effective dose of bimakalim or derivative over the multi-day administration period.

2. The patch of claim 1 wherein the backing layer is elastomeric.

3. The patch of claim 1 wherein the reservoir layer has a basal surface that defines the drug-delivery area.

4. The patch of claim 3 wherein the drug-delivery area is 3 to 100 $cm^2$.

5. The patch of claim 1 wherein the flux is in the range of about 0.1 to about 4 $\mu g/cm^2/hr$.

6. The patch of claim 1 wherein the patch is able to administer the bimakalim or derivative for about 3 to 7 days.

7. The patch of claim 1 wherein the reservoir includes an additive that increases the solubility of the bimakalim or derivative in the adhesive and/or enhances permeability of skin to the bimakalim or derivative.

8. The patch of claim 7 wherein the additive is propylene glycol monolaurate, propylene glycol, methyl laurate, vegetable oil, or silicone oil.

9. The patch of claim 8 wherein the adhesive is a polydimethylsiloxane adhesive.

10. The patch of claim 1 wherein the adhesive is a polydimethylsiloxane adhesive or an acrylate adhesive.

11. The patch of claim 1 wherein the condition is cardiovascular disease.

* * * * *